(12) United States Patent
Bosser

(10) Patent No.: US 12,083,002 B2
(45) Date of Patent: Sep. 10, 2024

(54) RETENTION DEVICE AND TAPE FOR RETENTION DEVICE

(71) Applicant: APLIX, Le Cellier (FR)

(72) Inventor: Damien Bosser, Le Cellier (FR)

(73) Assignee: APLIX, Le Cellier (FR)

( * ) Notice: Subject to any disclaimer, the term of this patent is extended or adjusted under 35 U.S.C. 154(b) by 1034 days.

(21) Appl. No.: 16/964,755

(22) PCT Filed: Jan. 25, 2019

(86) PCT No.: PCT/FR2019/050163
§ 371 (c)(1),
(2) Date: Jul. 24, 2020

(87) PCT Pub. No.: WO2019/145647
PCT Pub. Date: Aug. 1, 2019

(65) Prior Publication Data
US 2020/0352800 A1    Nov. 12, 2020

(30) Foreign Application Priority Data

Jan. 26, 2018 (FR) ...................................... 1850645

(51) Int. Cl.
*A44B 18/00* (2006.01)
*A61F 13/62* (2006.01)
*A61F 13/84* (2006.01)

(52) U.S. Cl.
CPC ........ *A61F 13/625* (2013.01); *A44B 18/0015* (2013.01); *A61F 2013/8497* (2013.01); *Y10T 428/24008* (2015.01); *Y10T 428/24017* (2015.01)

(58) Field of Classification Search
None
See application file for complete search history.

(56) References Cited

U.S. PATENT DOCUMENTS

| | | | |
|---|---|---|---|
| 2005/0060849 | A1 | 3/2005 | Vanbenschoten et al. |
| 2014/0338159 | A1 | 11/2014 | Sakaguchi et al. |
| 2014/0358107 | A1 | 12/2014 | Bader et al. |
| 2016/0128877 | A1 | 5/2016 | Chandrasekaran et al. |

FOREIGN PATENT DOCUMENTS

| | | |
|---|---|---|
| CN | 101959436 A | 1/2011 |
| CN | 102946753 A | 2/2013 |
| CN | 103796622 A | 5/2014 |

(Continued)

OTHER PUBLICATIONS

Notice of Reasons for Refusal issued in corresponding Japanese Application No. 2020-560605 dated Nov. 9, 2022, with English Translation (20 pages).

(Continued)

*Primary Examiner* — Alexander S Thomas
(74) *Attorney, Agent, or Firm* — Bookoff McAndrews, PLLC

(57) ABSTRACT

A retention device (10) includes a continuous base (12) having an upper face (12A) and a lower face (12B) and extending in a longitudinal direction and a plurality of retention elements (16) extending from the upper face (12A) of the base (12), each retention element (16) including a rod (18). The base (12) includes at least one zone (20) free of retention elements so that the plurality of retention elements (16) form at least one pattern (14).

19 Claims, 9 Drawing Sheets

(56) References Cited

FOREIGN PATENT DOCUMENTS

| | | |
|---|---|---|
| CN | 105392457 A | 3/2016 |
| FR | 3050620 A1 | 11/2017 |
| JP | 2005073897 A | 3/2005 |
| JP | 2009119201 A | 6/2009 |
| JP | 2010-507397 A | 3/2010 |
| JP | 2013-063165 A | 4/2013 |

OTHER PUBLICATIONS

Notice of Reasons for Refusal issued in corresponding Japanese Application No. 2020-560606 dated Nov. 9, 2022, with English Translation (20 pages).

Official Action and Search Report in Chinese Patent Application No. 201980010371.9 dated Jul. 13, 2021, with English translation (19 pages).

Notice of Reasons for Refusal issued in Japanese application No. 2020-560605, dated May 2, 2023.

International Search Report issued in International Application No. PCT/FR2019/050162, dated Apr. 11, 2019, with English translation (6 pages).

International Search Report issued in International Application No. PCT/FR2019/050163, dated Jun. 5, 2019, with English translation (7 pages).

Paillasson d'extérieur en pin lazuré et poils en nylon, Nov. 3, 2016, retrieved from Internet at https://www.landmade.fr/boutique/pelles-et-paillas ons/41-paillass n-40x60.html, with English translation (6 pages).

RETENTION DEVICE AND TAPE FOR RETENTION DEVICE

CROSS-REFERENCE TO RELATED APPLICATION(S)

This application is the U.S. national phase entry under 35 U.S.C. § 371 of International Application No. PCT/FR2019/050163, filed on Jan. 25, 2019, which claims priority to French Patent Application No. 1850645, filed on Jan. 26, 2018.

TECHNOLOGICAL FIELD

The present disclosure relates to a retention device including protruding elements, such as rods and/or preforms and/or hooks, for example intended to cooperate with a hook and/or loop counterpart.

TECHNOLOGICAL BACKGROUND

In particular in the field of hygiene, retention devices, for example with hooks, are used and cooperate with a loop counterpart forming an application zone of the retention device.

When a user positions the retention device on this application zone, the user may doubt that he has correctly positioned the retention device on the application zone. This application zone is commonly called in the field of "comfort web" hygiene or identified by the expression "landing zone". The fact that the user is sure that he has correctly positioned the retention device on the application zone will affect the perception that the user has due to the fact that the retention device is properly maintained on the application zone.

The user may also have to reposition the retention device on the application zone, for example in order to better adjust the item and/or to remove the item.

The peeling force is typically the force that the user will exert on the retention device to separate the retention device from the application zone. The ease with which the user can separate the retention device from the application zone will affect the perception that the user has due to the fact that the retention device is properly maintained on the application zone. In some extreme cases, a low peeling force can cause an unexpected detachment of the retention device and of the application zone.

There is therefore a need to improve the actual feeling/quality and/or the feeling/quality perceived by the user when he uses the retention device in a closing and/or opening manner.

PRESENTATION

The present disclosure aims at least partially at overcoming these drawbacks by proposing a retention device which is simple to use, visual, cognitive and intuitive for the user.

To this end, according to a first aspect, the present disclosure relates to a retention device including:
a continuous base having an upper face and a lower face; and
a plurality of retention elements extending from the upper face of the base, each retention element including a rod; the base including at least one zone free of retention elements so that the plurality of retention elements form at least one pattern, and in a CIE L*a*b* color space, a color difference ΔE* between the at least one zone free of retention elements and at least part of the pattern formed by the plurality of retention elements is greater than or equal to 1.0, preferably greater than or equal to 1.5, even more preferably greater than or equal to 3.0, even more preferably greater than or equal to 4.5.

By "pattern", it is understood that the distribution of the retention elements is not uniform over the entire base. Thus, although the retention elements may be spaced uniformly on the base to form the pattern, some zones of the base are free of retention elements and allow delimiting the pattern.

The pattern includes a pattern surface corresponding to the surface covered by circles of radius corresponding to the average pitch and whose center of each circle is positioned respectively, when viewed from above, on the center of the retention elements and the circumference of each circle passes through the center of at least one adjacent retention element. The average pitch may correspond to the distance separating two adjacent retention elements. The at least one zone free of retention elements is the surface not covered by the pattern surface.

The color difference ΔE* between the zones free of retention elements and at least part of the pattern formed by the plurality of retention elements is greater than or equal to 1.0, the user may visually identify the pattern formed by the plurality of retention elements and therefore be certain that he is properly positioning the pattern on an application zone, such as a loop counterpart for example. This allows therefore improving the actual feeling/quality and/or the feeling/quality perceived by the user when he uses the retention device in a closing and/or opening manner.

The CIE L*a*b* color space or CIE L*a*b* chromatic space, generally called CIELAB, is the most widely used space and is issued by the International Commission on Illumination (CIE) in order to characterize surface colors. This space describes all the colors visible to the human eye and was created to be used as a reference. In this space, the clarity L* varies from 0 (=black) to 100 (=white), the parameter a* represents the value on an axis varying from green to red and the parameter b* represents the value on an axis varying from blue to yellow. The color difference ΔE* between the zones free of retention elements and at least part of the pattern formed by the plurality of retention elements is calculated according to equation (1):

$$\Delta E^* = \sqrt{\Delta L^{*2} + \Delta a^{*2} + \Delta b^{*2}} \qquad (1)$$

The values of L*, a* and b* are measured for example with a spectrocolorimeter in natural light (under the reference D65/10°) of model RM200QC of x-rite pantone on a white support. This spectrometer is particularly well adapted to measure surfaces greater than or equal to 4 mm².

In some embodiments, there are several zones provided with retention elements, each zone provided with retention elements having, in the CIE L*a*b* color space, a color difference ΔE* between the at least one zone free of retention elements and at least part of the pattern formed by the plurality of retention elements, the color difference ΔE* being greater than or equal to 1.0, preferably greater than or equal to 1.5, even more preferably greater than or equal to 3.0 still more preferably greater than or equal to 4.5.

In some embodiments, there are several zones provided with retention elements, each zone provided with retention elements having, in the CIE L*a*b* color space, a color difference ΔE* between a first zone provided with retention elements and a second zone provided with retention elements, the color difference ΔE* being greater than or equal to 1.0, preferably greater than or equal to 1.5, even more preferably greater than or equal to 3.0 even more preferably greater than or equal to 4.5.

In some embodiments, the retention element includes the rod surmounted by a head.

The rod includes a lower end bonded to the base, and an upper end opposite to the lower end and the head surmounts the upper end of the rod.

This type of retention element may for example be a preform and/or a hook.

In some embodiments, a surface of the zones free of retention elements is greater than or equal to 5% of a total surface of the base, preferably greater than or equal to 10%, even more preferably greater than or equal to 15%.

Generally, the retention elements are not present on the edges of the base. Thus, for retention devices not including a pattern, that is to say retention devices in which the retention elements are distributed uniformly over the entire base, there may be a web, along the edges of the base free of retention elements. However, these webs do not have a sufficient surface to allow identification by the user of a pattern due to their straight shape. The user therefore does not identify the presence of zones free of retention elements as zones delimiting a pattern. It is understood that the narrow zones generally forming a web on the edge of the retention device are not bordered on each side by retention devices.

In some embodiments, the pattern is a single pattern.

It is meant by "single pattern" a pattern isolated in a zone of the base measuring 25.4 mm or 30.0 mm or 35.0 mm in the MD direction and 13.0 mm or 25.0 mm or 25.4 mm in the CD direction.

It is meant by "MD direction" in accordance with the acronym for "Machine Direction" the direction of movement of the base in the machine during the manufacture of the retention device, and by "CD direction" in accordance with the acronym for "Cross Direction", the direction perpendicular to the MD direction.

This pattern may for example have a pattern recognizable by the user, for example a distinctive sign or a trademark.

In some embodiments, the pattern is a repeating pattern.

The pattern may for example be of smaller dimension, compared to a single pattern, but may be repeated several times.

In some embodiments, the repeated pattern may be a complex pattern.

It is meant by "complex pattern" a pattern including several entities which may be different from each other, this complex pattern being itself repeated at least once.

In some embodiments, the pattern has a closed contour.

It is meant by "closed contour" a curve whose both ends coincide.

In some embodiments, the pattern is arranged so that when the retention device is biased in an opening manner, a force exerted on the retention device is divided between at least a first component into peeling force and a second component into shear force.

In some embodiments, in a CIE XYZ color space, the difference in opacity between the at least one zone free of retention elements and at least part of the pattern formed by the plurality of retention elements is greater than or equal to 1, preferably greater than or equal to 2, even more preferably greater than or equal to 3.

The CIE XYZ color space is a color space defined by the International Commission on Illumination. The component Y of the CIE XYZ space corresponds to the luminance that is to say to the luminosity of a surface. According to the standard ASTM D2805, the opacity expressed in percent is calculated according to the equation (2):

$$\text{Opacity (\%)} = Y_{black\ background}/Y_{white\ background} * 100 \quad (2)$$

where $Y_{black\ background}$ is the measurement of Y performed on a black support and $Y_{white\ background}$ is the measurement of Y performed on a white support.

The values of $Y_{black\ background}$ and $Y_{white\ background}$ are measured for example with a spectrocolorimeter in natural light (under the reference D65/10°) of model RM200QC of x-rite pantone on a white support and on a black support.

The difference in opacity between the zones free of retention elements and at least part of the pattern formed by the plurality of retention elements is equal to the absolute value of the difference in opacity values obtained for the zone free of retention elements and for at least part of the pattern formed by the plurality of retention elements.

In some embodiments, there are several zones provided with retention elements, each zone provided with retention elements having, in the CIE XYZ color space, a difference in opacity between the at least one zone free of retention elements and at least part of the pattern formed by the plurality of retention elements, the opacity difference being greater than or equal to 1, preferably greater than or equal to 2, even more preferably greater than or equal to 3.

In some embodiments, there are several zones provided with retention elements, each zone provided with retention elements having, in the CIE XYZ color space, a difference in opacity between a first zone provided with retention elements and a second zone provided with retention elements, the opacity difference being greater than or equal to 1, preferably greater than or equal to 2, even more preferably greater than or equal to 3.

In some embodiments, the base and the plurality of retention elements are made of thermoplastic material.

As a non-limiting example of a thermoplastic material, mention may be made of a polyolefin, polyethylene, LLDPE (Linear Low Density PolyEthylene), LDPE (Low Density PolyEthylene), m-PE (MetallocenePolyEthylene), HDPE (High Density PolyEthylene), EVA (Ethylene Vinyl Acetate) and PP (PolyPropylene), including a distribution of a monomodal or multimodal (for example bimodal) molecular weight, particularly a composition including LLDPE and of a plastomer, in particular a polyethylene-based plastomer. Polyamide (PA), polylactic acid (PLA), polyhydroxyalkanoates (PHA), PVOH, PBS, polyester, polyvinyl chloride (PVC) or acrylonitrile butadiene styrene (ABS) could also be used.

In some embodiments, the base and the plurality of retention elements are made of thermoplastic material including a dye.

The dye may for example be a white dye, for example mention may be made of the reference 50PP marketed by CABOT and which is loaded with 50% by mass of $TiO_2$. As another dye, mention may also be made of the reference UN55206 manufactured by COLOR SERVICE. These examples are given as non-limiting examples.

The dye allows increasing the visual contrast between the zones free of retention elements and the pattern formed by the plurality of retention elements.

In some embodiments, the base and the plurality of retention elements are made of thermoplastic material including at most 2% by mass of dye, preferably at most 1.5% by mass, even more preferably at most 1% by mass of dye.

In some embodiments, one end of each retention element farthest from the base includes a colored coating.

Thus, a colored coating may be deposited, for example an ink or a dye, such as those commonly used in flexography and/or pad printing and/or rotogravure and/or serigraphy and/or heliography, in order to deposit the colored coating on the end of each retention element farthest from the base. The ink may be a solvent-based or water-based ink or ultraviolet cross-linkable.

An ink is generally composed of a mixture of three components: a coloring matter, in particular a pigment or a dye; a vehicle forming the fluid phase of the ink, for example a mixture of polymers, diluents and/or solvent or water; and additives, such as dispersing and anti-foaming agents etc., making it possible to optimize the characteristics of the ink.

As a mixture of polymers, it is possible to use mixtures including for example up to 50% by mass of various acetates, such as the ethyl acetate, N-propyl acetate, isopropyl acetate, N-butyl acetate, and mixtures thereof and/or up to 10% by mass of alcohol.

Organic or mineral pigments may be used, such as, for example, diazo dyes, anthraquinone dyes, xanthene, azine and the like, titanium dioxide, carbon black, iron oxides, chromium oxide and the like.

As a non-limiting example of ink, it is possible to use an ink marketed by ULTRA ink under the reference "Type Series 30,000 ALC polyamide" or an ink marketed by the company DOMECK EUROFLEX under the reference "Type Series EURO-Film PXA".

It is understood that this colored coating may be deposited on an uncolored or colored thermoplastic material, in order to increase the contrast between the zones free of retention elements and the pattern formed by the plurality of retention elements.

Typically, an inking roller is coated with ink or dye and the retention device is driven so that only the retention elements are brought into contact with the inking roller. The end farthest from the base of each retention element will thus be covered with a colored coating for accentuating the visibility of the pattern.

In some embodiments, the pattern is repetitive in a peeling direction, the peeling force measured according to the "180° peeling" method has at least two peaks and at least one valley comprised between the two peaks, maximum values of the peaks increasing with the opening stroke and the at least one valley having a minimum value less than or equal to 85% of a maximum value of the peeling force, preferably less than or equal to 70%, even more preferably less than or equal to 60%, even more preferably less than or equal to 50%, even more preferably less than or equal to 40%.

The "180° peeling" method is a method which allows measuring the peeling force, that is to say the force to separate the retention device and the application zone. This method is described below.

Conditioning of the samples—The samples to be tested are conditioned for 2 h (hour) at 23° C.+/−2° C. with a relative moisture of 50%+/−5%.

Preparation of the retention device—The retention device is generally used in the CD direction. The retention device is generally in the form of a tape whose length is in the MD direction. Part of the tape in the MD direction is glued on a paper of 80 g/cm$^2$ and a roller of 2 kg (kilogram) is applied or rotated on the retention device in one direction and then in the other (round trip) over the entire length of the part of the tape. The paper and the retention device are cut using a pair of scissors into strips of a width of 25.4 mm (millimeter) in the CD direction at a speed of approximately 700 mm/min (millimeter per minute). Each paper strip has a length of 210 mm and the retention device is disposed in the center of this strip.

Preparation of the application zone—The sample from the application zone has a width of 50 mm in the MD direction and the length is at most of 200 mm and the sample is cut in half depending on the length.

Assembly—The strip is disposed on the sample from the application zone so that the retention device is centered on the sample from the application zone. The 2 kg (kilogram) roller is applied or rotated on the strip in one direction and then in the other (round trip) over the entire length of the strip at a speed of about 700 mm/min. The sample from the application zone is disposed in a clamp of a gallows, the cut side being in the clamp and a weight of 1 kg is suspended on the lower part of the strip for 10 s (second). The weight is then removed. This step allows ensuring the correct assembly of the retention device and of the sample from the application zone.

Measurement—The assembly is then disposed in a tensile-testing machine including a 100 N (newton) measuring cell. The strip is inserted into the upper (movable) jaw. The reading of the force measuring cell is set to zero. The sample from the application zone is inserted into the lower (fixed) jaw and a slight tension is created. The force must be comprised between 0.02 N and 0.05 N. During installation, the jaws are spaced apart from each other by 50 mm. The assembly is centered between the two jaws. The test is carried out at constant movement at a speed of 305 mm/min and the test stroke is of 50 mm. This test stroke is adapted according to the width of the retention device to be tested.

It is understood that the valley is located between two successive peaks. Since the peeling curves are not smooth, in order to differentiate one peak from another, it is considered that there is a new peak when the difference in maximum value of two peaks is at least 10% of the maximum value of the largest force measured, that is to say greater than 10% of the maximum value of the largest peak. The peaks and valleys have a tip and a base, the base may have a width preferably greater than 1 mm, more particularly a width greater than 2 mm, in some cases, a width greater than 3 mm.

Thanks to the peeling force which has at least two consecutive peaks separated by a valley, the value of the peaks of the peeling force increasing with the opening stroke, the user feels this increasing force required to separate the retention device of the application zone. He therefore perceives that the retention device was well maintained on the application zone. Furthermore, the maximum value of the peeling force is such that the retention device may not be detached from the application zone in an undesired manner.

It is generally considered that a peeling force, obtained according to the "180° peeling" method, which is greater than or equal to 1.8 N allows avoiding an unexpected detachment of the retention device and of the application zone and this regardless of the retention device and of the application zone.

In some embodiments, the pattern is repetitive in a peeling direction, the peeling force measured according to the "180° peeling" method has at least three peaks and at least two valleys, each valley being comprised between two consecutive peaks, the maximum values of the peaks increasing with the opening stroke and the valleys having a minimum value less than or equal to 85% of a maximum value of the peeling force, preferably less than or equal to 70%, even more preferably less than or equal to 60%, even more preferably less than or equal to 50%, even more preferably less than or equal to 40%.

In some embodiments, the device includes zones free of retention elements that are continuous in a direction perpendicular to the peeling direction.

In some embodiments, the zones free of retention elements which are continuous in a direction perpendicular to the peeling direction have a width measured in the peeling direction greater than or equal to 2 rows of measured retention elements in the peeling direction, preferably greater than or equal to 3 rows of measured retention elements in the peeling direction.

Although these continuous zones free of retention elements have a small width, they allow defining a pattern formed by the retention elements because they are bordered on each side by retention elements.

In some embodiments, the zones free of retention elements that are continuous in a direction perpendicular to the peeling direction have a width measured in the peeling direction greater than or equal to 1% of the width of the base measured in the peeling direction, preferably greater than or equal to 2%, preferably greater than or equal to 4%, even more preferably greater than or equal to 5%, even more preferably greater than or equal to 10%.

In some embodiments, the retention device includes a woven or non-woven web or a thermoplastic film or an elastic film or a composite film.

This woven or non-woven web or the thermoplastic film or the elastic film or the composite film serves as support for the base.

It is meant by "non-woven" a product obtained at the end of the formation of a lap of fibers and/or filaments that have been consolidated. The consolidation may be mechanical, chemical or thermal and results in the presence of a bond between the fibers and/or the filaments. This consolidation may be direct, that is to say made directly between the fibers and/or filaments by welding, or it may be indirect, that is to say by means of an intermediate layer between the fibers and/or the filaments, for example a layer of glue or a layer of binder. The term "non-woven" refers to a structure in the form of a tape or a lap of fibers and/or filaments that are intertwined in a non-uniform, uneven or random manner. A non-woven may have a single-layer structure or a multi-layer structure. A non-woven may also be combined with another material to form a laminate. A non-woven may be made from different synthetic and/or natural materials. Natural materials by way of example are cellulose fibers, such as cotton, jute, linen, and the like, and may also include re-treated cellulose fibers, such as rayon or viscose. The natural fibers for a non-woven material may be prepared using various methods such as carding. By way of examples, synthetic materials include, but are not limited to, synthetic plastic polymers, which are known to form fibers that include, but are not limited to, polyolefins, for example polyethylene, polypropylene, polybutylene and the like; polyamide, for example polyamide 6, polyamide 6.6, polyamide 10, polyamide 12 and the like; polyesters, for example polyethylene terephthalates, polybutylene terephthalates, polylactic acids and the like, polycarbonates, polystyrenes, thermoplastic elastomers, vinyl polymers, polyurethanes and mixtures and co-polymers thereof. By way of example, the non-woven may be a non-woven of the type Spunbond, Spunmelt, carded thermally-bonded, SMS, SMMS, SS, SSS, SSMMS, SSMMMS, Air through or the like. For example, the non-woven may be a non-woven including a different combination of layers of Spunbond "S" and of Meltblown "M". These examples are given as non-limiting examples.

The web is not limited to a non-woven, and may be more generally a woven material, a knitted material, or a combination of several of these materials.

It is meant by "thermoplastic film" a film made of thermoplastic material which may be an elastic material or a non-elastic material.

It is meant by "thermoplastic film made of elastic material" a film which may be stretched without breaking under the effect of a stretching force exerted in the lateral direction and which may substantially recover its shape and its initial dimensions after relaxing this stretching force. It is for example a film that retains a residual deformation or remanence after elongation and relaxing (residual deformation also called permanent set or SET) of less than 20%, more preferably less than 5%, of its initial dimension (before elongation) for an elongation of 100% of its initial dimension, at room temperature (23° C.).

It is meant by "thermoplastic film made of non-elastic material" a film that does not fall within the definition of a thermoplastic film made of elastic material.

In some embodiments, the base is overmolded on the web.

In some embodiments, the base has a thickness, measured perpendicularly to the upper face of the base, greater than or equal to 10 µm, preferably greater than or equal to 50 µm and less than or equal to 700 µm, preferably less than or equal to 500 µm, even more preferably less than or equal to 100 µm.

In some embodiments, the base may have a constant or non-constant thickness between two opposite edges of the base, for example between two opposite edges extending in the CD or MD direction. The base may be continuous or discontinuous between two opposite edges of the base, for example between two opposite edges extending in the CD or MD direction.

In some embodiments, a height of the retention elements, measured perpendicularly to the upper face of the base is comprised between 3 and 10 times the thickness of the base.

In some embodiments, the base has a thickness, measured perpendicularly to the upper face of the base, comprised between 10 and 700 µm and a height of retention elements, measured perpendicularly to the upper face of the base, comprised between 3 and 10 times the thickness of the base.

In some embodiments, the height of the retention elements is greater than or equal to 35 µm, preferably greater than or equal to 55 µm, even more preferably greater than or equal to 80 µm and less than or equal to 500 µm, preferably less than or equal to 350 µm, even more preferably less than or equal to 120 µm.

For example, the height of the retention elements may be comprised between 80 and 350 µm or between 55 and 120 µm.

In some embodiments, the diameter in which the retention element is inscribed (in top view, perpendicularly to the retention element) is greater than or equal to 80 µm, preferably greater than or equal to 250 µm and less than or equal to 500 µm, preferably less than or equal to 450 µm.

In some embodiments, a minimum distance between two retention elements is comprised between 0.1 mm and 10 mm.

In some embodiments, the pattern has a density of retention elements greater than or equal to 20 retention elements per $cm^2$, preferably greater than or equal to 50 retention elements per $cm^2$, even more preferably greater than or equal to 100 retention elements per $cm^2$ and less than or equal to 250 retention elements per cm$^2$, preferably less than or equal to 200 retention elements per cm$^2$, even more preferably less than or equal to 150 retention elements per cm$^2$.

According to a second aspect, the present disclosure also relates to a retention device including:
- a continuous base having an upper face and a lower face; and
- a plurality of retention elements extending from the upper face of the base, each retention element including a rod;
- the base including at least one zone free of retention elements so that the plurality of retention elements forms at least one pattern and wherein the pattern is repetitive in a peeling direction, the peeling force measured according to the "180° peeling" method having at least two peaks and at least one valley comprised between the two peaks, maximum values of the peaks increasing with the opening stroke and the at least one valley having a minimum value less than or equal to 85% of a maximum value of the peeling force, preferably less than or equal to 70%, even more preferably less than or equal to 60%, even more preferably less than or equal to 50%, even more preferably less than or equal to 40%.

By "pattern", it is understood that the distribution of the retention elements is not uniform over the entire base. Thus, although the retention elements may be uniformly spaced on the base to form the pattern, some zones of the base are free of retention elements and make it possible to delimit the pattern.

The pattern includes a pattern surface corresponding to the surface covered by circles of radius corresponding to the average pitch and whose center of each circle is positioned respectively, when viewed from above, on the center of the retention elements. The average pitch may correspond to the distance separating two adjacent retention elements. The at least one zone free of retention elements is the surface not covered by the pattern surface.

Thanks to the peeling force which has at least two consecutive peaks separated by a valley, the value of the peaks of the peeling force increasing with the opening stroke, the user feels this increasing force required to separate the retention device from the application zone. He therefore perceives that the retention device was properly maintained on the application zone. Furthermore, the maximum value of the peeling force is such that the retention device may not be detached from the application zone in an undesired manner. This allows therefore improving the actual feeling/quality and/or the feeling/quality perceived by the user when he uses the retention device in a closing and/or opening manner.

The peaks and valleys have a tip and a base, the base may have a width preferably greater than 1 mm, more particularly a width greater than 2 mm, in some cases, a width greater than 3 mm.

It is generally considered that a peeling force, obtained according to the "180° peeling" method, which is greater than or equal to 1.8 N allows avoiding an unexpected detachment of the retention device and of the application zone and this, regardless of the retention device and of the application zone.

In some embodiments, the pattern is repetitive in a peeling direction, the peeling force measured according to the "180° peeling" method has at least three peaks and at least two valleys, each valley being comprised between two consecutive peaks, the maximum values of the peaks increasing with the opening stroke and the valleys having a minimum value less than or equal to 85% of a maximum value of the peeling force, preferably less than or equal to 70%, even more preferably less than or equal to 60%, even more preferably less than or equal to 50%, even more preferably less than or equal to 40%.

In some embodiments, the device includes zones free of retention elements that are continuous in a direction perpendicular to the peeling direction.

In some embodiments, the zones free of retention elements that are continuous in a direction perpendicular to the peeling direction have a width measured in the peeling direction greater than or equal to 2 rows of retention elements measured in the peeling direction, preferably greater than or equal to 3 rows of retention elements measured in the peeling direction.

In some embodiments, the zones free of retention elements that are continuous in a direction perpendicular to the peeling direction have a width measured in the peeling direction greater than or equal to 1% of the width of the base measured in the peeling direction, preferably greater than or equal to 2%, preferably greater than or equal to 4%, even more preferably greater than or equal to 5%, still more preferably greater than or equal to 10%.

In some embodiments, in a CIE L*a*b* color space, a color difference ΔE* between the at least one zone free of retention elements and at least part of the pattern formed by the plurality of retention elements is greater than or equal to 1.0, preferably greater than or equal to 1.5, even more preferably greater than or equal to 3.0 even more preferably greater than or equal to 4.5.

In some embodiments, there are several zones provided with retention elements, each zone provided with retention elements having, in the CIE L*a*b* color space, a color difference ΔE* between the at least one zone free of retention elements and at least part of the pattern formed by the plurality of retention elements, the color difference ΔE* being greater than or equal to 1.0, preferably greater than or equal to 1.5, even more preferably greater than or equal to 3.0 even more preferably greater than or equal to 4.5.

In some embodiments, there are several zones provided with retention elements, each zone provided with retention elements having, in the CIE L*a*b* color space, a color difference ΔE* between a first zone provided with retention elements and a second zone provided with retention elements, the color difference ΔE* being greater than or equal to 1.0, preferably greater than or equal to 1.5, even more preferably greater than or equal to 3.0 even more preferably greater than or equal to 4.5.

In some embodiments, the retention device includes the rod surmounted by a head.

In some embodiments, a surface of the zones free of retention elements is greater than or equal to 5% of a total surface of the base, preferably greater than or equal to 10%, even more preferably greater than or equal to 15%.

In some embodiments, the pattern is a single pattern.

It is meant by "single pattern" an isolated pattern in a zone of the base measuring 25.4 mm or 30.0 mm or 35.0 mm in the MD direction and 13.0 mm or 25.0 mm or 25.4 mm in the CD direction.

This pattern may for example represent a pattern recognizable by the user, for example a distinctive sign or a trademark.

In some embodiments, the pattern is a repeating pattern.

In some embodiments, the repeated pattern may be a complex pattern.

In some embodiments, the pattern has a closed contour.

In some embodiments, the pattern is arranged so that when the retention device is biased in an opening manner, a force exerted on the retention device is divided between at least a first component into peeling force and a second component into shear force.

In some embodiments, in a CIE XYZ color space, the difference in opacity between the zones free of retention elements and at least part of the pattern formed by the plurality of retention elements is greater than or equal to 1, preferably greater than or equal to 2, even more preferably greater than or equal to 3.

In some embodiments, there are several zones provided with retention elements, each zone provided with retention elements having, in the CIE XYZ color space, a difference in opacity between the at least one zone free of retention elements and at least part of the pattern formed by the plurality of retention elements, the opacity difference being greater than or equal to 1, preferably greater than or equal to 2, even more preferably greater than or equal to 3.

In some embodiments, there are several zones provided with retention elements, each zone provided with retention elements having, in the CIE XYZ color space, a difference in opacity between a first zone provided with retention elements and a second zone provided with retention elements, the opacity difference being greater than or equal to 1, preferably greater than or equal to 2, even more preferably greater than or equal to 3.

In some embodiments, the base and the plurality of retention devices are made of thermoplastic material.

In some embodiments, the base and the plurality of retention devices are made in one piece.

In other words, the base and the plurality of retention elements are made of the same material and in this material there is no interface at the junction between the base and the plurality of retention elements.

In some embodiments, the base and the plurality of retention elements are made of thermoplastic material including a dye.

In some embodiments, the base and the plurality of retention elements are made of thermoplastic material including at most 2% by mass of dye, preferably at most 1.5% by mass, even more preferably at most 1% by mass of dye.

In some embodiments, one end of each retention device farthest from the base includes a colored coating.

In some embodiments, the retention device includes a woven or non-woven web or a thermoplastic film or an elastic film or a composite film.

In some embodiments, the base is overmolded on the web.

In some embodiments, the base has a thickness, measured perpendicularly to the upper face of the base, greater than or equal to 10 µm, preferably greater than or equal to 50 µm and less than or equal to 700 µm, preferably less than or equal to 500 µm, even more preferably less than or equal to 100 µm.

In some embodiments, the base may have a constant or non-constant thickness between two opposite edges of the base, for example between two opposite edges extending in the CD or MD direction. The base may be continuous or discontinuous between two opposite edges of the base, for example between two opposite edges extending in the CD or MD direction.

In some embodiments, a height of the retention elements, measured perpendicularly to the upper face of the base is comprised between 3 and 10 times the thickness of the base.

In some embodiments, the base has a thickness, measured perpendicularly to the upper face of the base, comprised between 10 and 700 µm and a height of retention elements, measured perpendicularly to the upper face of the base, comprised between 3 and 10 times the thickness of the base.

In some embodiments, the height of the retention elements is greater than or equal to 35 µm, preferably greater than or equal to 55 µm, even more preferably greater than or equal to 80 µm and less than or equal to 500 µm, preferably less than or equal to 350 µm, even more preferably less than or equal to 120 µm.

For example, the height of the retention elements may be comprised between 80 and 350 µm or between 55 and 120 µm.

In some embodiments, the diameter in which the retention element is inscribed (in top view, perpendicularly to the retention element) is greater than or equal to 80 µm, preferably greater than or equal to 250 µm and less than or equal to 500 µm, preferably less than or equal to 450 µm.

In some embodiments, a minimum distance between two retention elements is comprised between 0.1 mm and 10 mm.

In some embodiments, the pattern has a density of retention elements greater than or equal to 20 per $cm^2$, preferably greater than or equal to 50 per $cm^2$, even more preferably greater than or equal to 100 per $cm^2$ and less than or equal to 250 per $cm^2$, preferably less than or equal to 200 per $cm^2$, even more preferably less than or equal to 150 per $cm^2$.

The present disclosure also relates to a tape for a retention device as defined above, the tape being intended to be cut into a plurality of retention devices.

BRIEF DESCRIPTION OF THE DRAWINGS

Other characteristics and advantages of the object of the present disclosure will emerge from the following description of embodiments, given by way of non-limiting examples, with reference to the appended figures, wherein.

In all of the figures, the elements in common are identified by identical reference numbers.

DETAILED DESCRIPTION

Figure 1A:
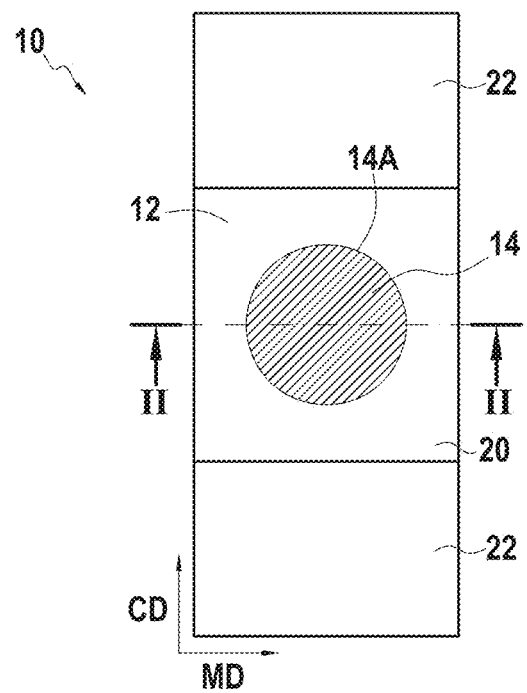
FIGS. 1A-1O are schematic representations of retention devices according to the present disclosure having different patterns.

FIG. 1A schematically represents a retention device 10 including a continuous base 12 and a pattern 14 in the form of a solid disk. As represented in FIG. 2, the base 12 includes an upper face 12A and a lower face 12B and the pattern 14 is formed by a plurality of retention elements 16 extending from the upper face 12A of the base 12. Each retention element 16 includes a rod 18. The base 12, particularly the upper face 12A of the base 12, also includes zones 20 free of retention elements 16. For reasons of simplification, the retention elements 16 are represented by hatching in FIGS. 1A to 1O and 6.

In the embodiment of FIG. 1A, the retention device 10 includes a non-woven (or woven) web 22. For example, the base 12 may be overmolded onto the non-woven web 22. The base 12 may also be glued on the non-woven web 22.

In the following, the elements common to the various embodiments are identified by the same reference numerals. Similarly, FIGS. 1B-1O show other embodiments of the retention device 10, particularly of the pattern 14 formed by the retention elements 16.

Figure 1B:
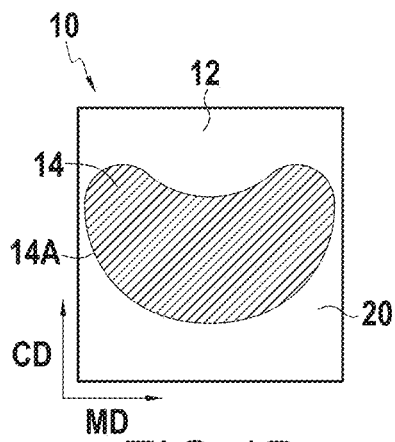
Figure 1C:
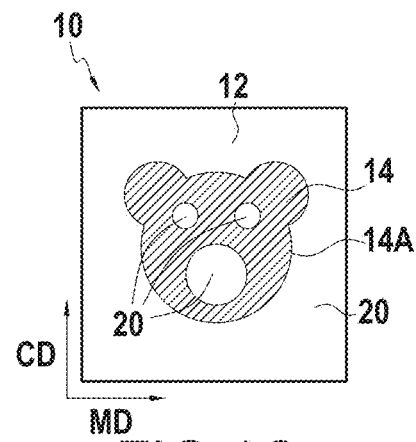
Figure 1D:
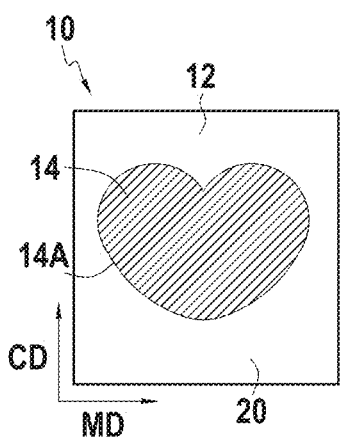
Figure 1E:
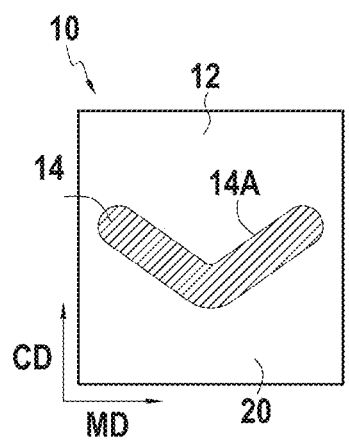
Figure 1F:
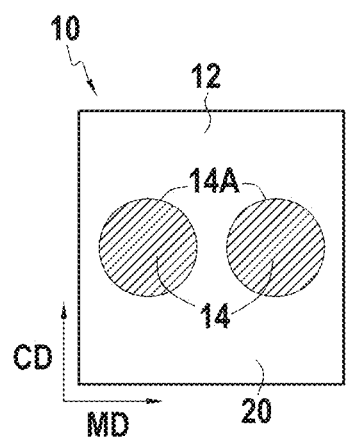
Figure 1G:
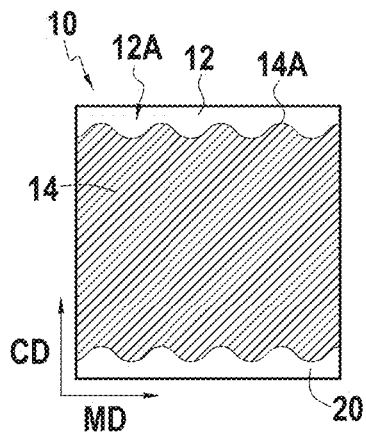
Figure 1H:
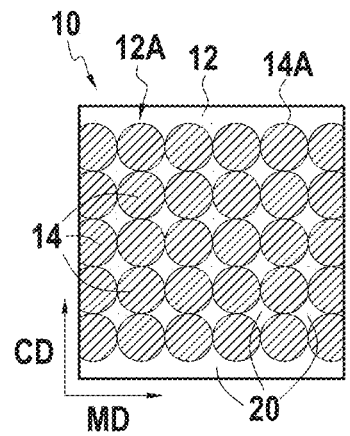
Figure 1I:
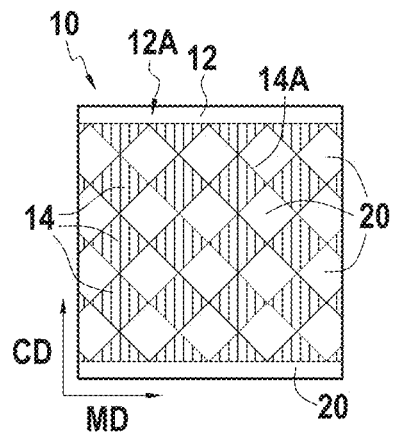
Figure 1J:
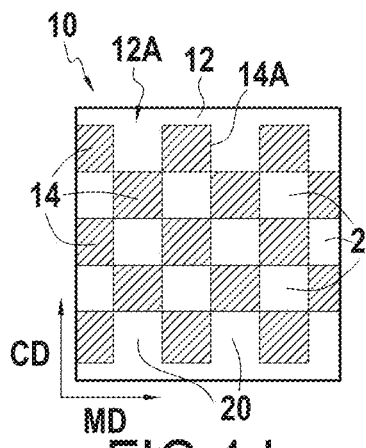
Figure 1K:
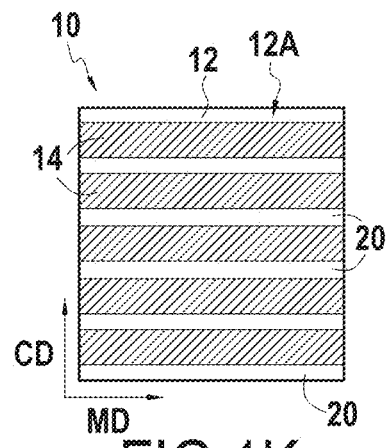
Figure 1L:
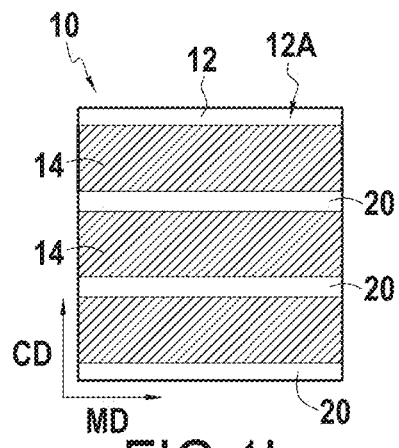
Figure 1M:
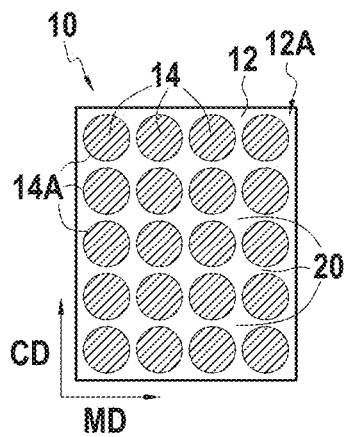
Figure 1N:
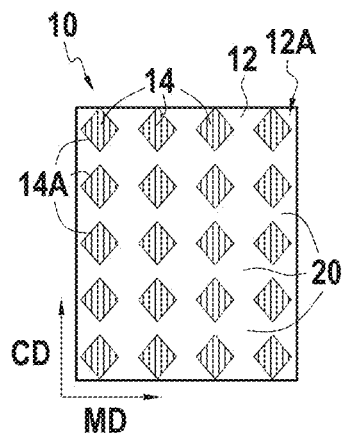
Figure 1O:
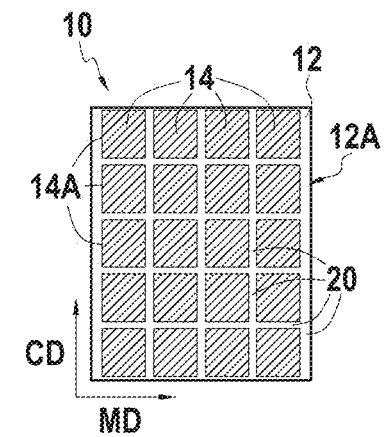
Figure 2:
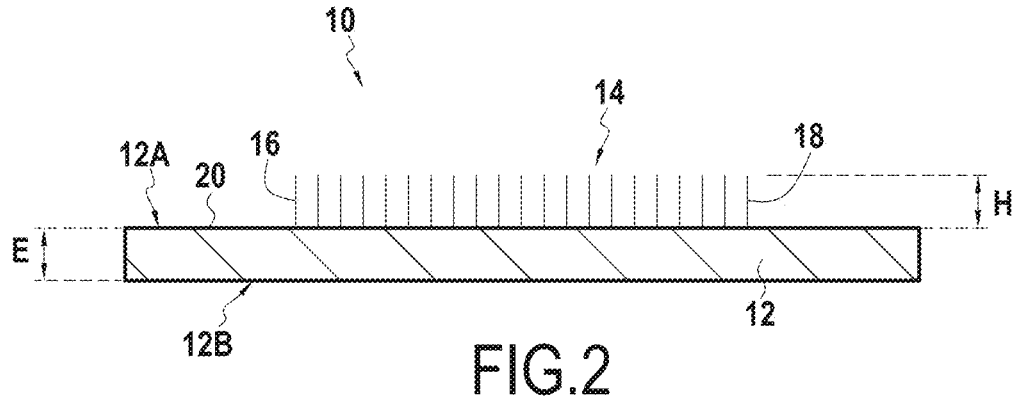
FIG. 2 is a sectional view of FIG. 1A along the section plane II-II.

As can be seen in FIGS. 1A-1B, the pattern 14 may be a single pattern (FIGS. 1A-1E and 1G) or a repeating pattern 14 (FIGS. 1F and 1H-1O). The pattern 14 may comprise a closed contour 14A (FIGS. 1A-1F, 1H-1J and 1M-1O).

It will be noted that in FIG. 1G, the zones 20 free of retention elements 16 are present on two edges of the retention device. However, these zones 20 have a corrugated edge which defines the pattern 14.

Figure 3:
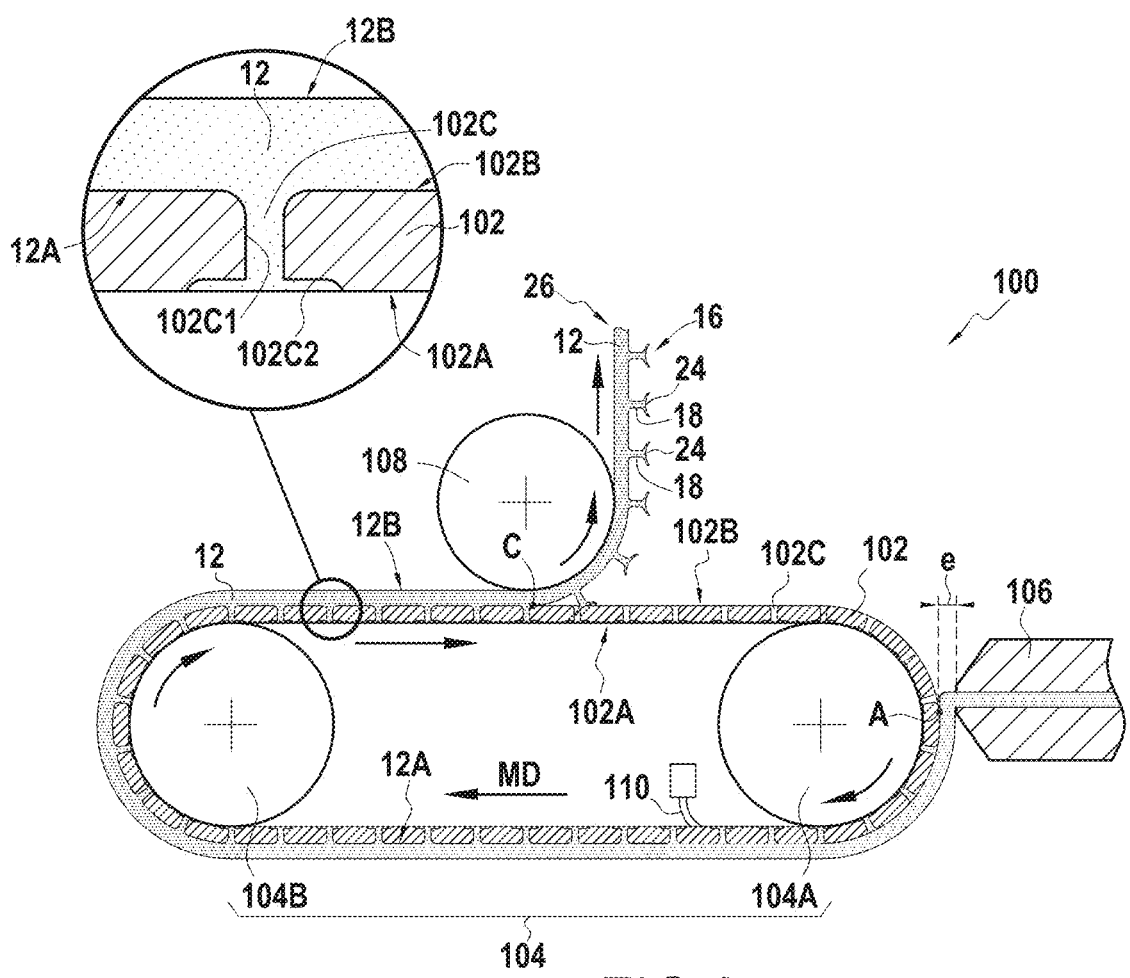
FIG. 3 is a schematic representation of an example of apparatus for producing a retention device.

As represented in FIG. 3, the retention elements 16 may comprise the rod 18 surmounted by a head 24. The rod 18 includes a lower end bonded to the base 12, and an upper end opposite to the lower end and the head 24 surmounts the upper end of the rod 18. The base 12 and the plurality of retention elements 16 are in one piece. It is therefore understood that the base 12 and the plurality of retention elements 16 are made of the same material and that in this material there is no interface at the junction between the base and the plurality of retention elements. This type of retention element 16 is generally designated by the term hook or preform which may then be modified, for example by calendering, to obtain a final hook. One example of a method for modifying the preform is described in document FR3050620 (incorporated by reference).

The retention device 10 may be manufactured for example by means of an apparatus 100 as represented in FIG. 3. The apparatus 100 allows manufacturing a tape 26 for a retention device, the tape 26 may then be cut into a plurality of retention devices 10. The tape 26 includes the continuous base 12 and a plurality of retention elements 16. In the embodiment of FIG. 3, the retention elements 16 are hooks, each hook including a rod 18 surmounted by a head 24.

The apparatus 100 as represented includes a molding web 102 positioned on rotational driving means 104 here including two rollers 104A, 104B, a material distribution means 106, for example an injector, adapted to carry out an injection of molding material, for example thermoplastic and/or elastic material.

The assembly formed by the molding web 102 and the rotational driving means 104 thus forms a molding device.

The example illustrated including two rollers 104A, 104B is not limiting, the number and the arrangement of the roller(s) may vary in particular in order to adapt to the length of the molding web 102 and to the different stations of the apparatus. It is possible for example to use three rollers or even only one so that the molding web is arranged on the periphery of the single roller to form a sleeve. Particularly, only one of the two rollers may be driven in rotation by motorized means, for example the roller 104A, the other roller 104B being free, that is to say without motorized means, and driven in rotation via the molding web, itself driven by the roller 104A.

The molding web 102 as presented includes an inner face 102A and an outer face 102B, the inner face 102A being in contact with the rotational driving means 104.

The material distribution means 106 is disposed so as to inject molding material on the outer face 102B of the molding web 102.

More specifically, the material distribution means 106 is disposed facing the molding web 102, spaced from the molding web 102 so as to define an air gap e indicated in FIG. 3. Reference A identifies the limit of the material injected on the outer face 102B of the molding web 102, corresponding to the rear front of the material injected on the molding web 102 relative to the direction of movement of the molding web 102.

The molding web 102 is provided with a plurality of cavities 102C that allow producing hooks of the hook retention device.

The cavities 102C are each formed so as to define a rod 102C1 extending from the outer face 102B towards the inner face 102A of the molding web 102 and a head 102C2 extending between the rod 102C1 and the inner face 102A of the molding web 102.

In the example illustrated, the heads 24 of the cavities 102C open out onto the inner face 102A of the molding web 102. The cavities 102C are therefore through cavities. Such an embodiment is not limiting, the cavities 102C may also be blind and therefore not open out from the inner face 102A of the molding web 102 and/or the cavities 102C may only include a rod 102C1.

The portions of the cavities 102C forming the rods 102C1 typically extend in a direction perpendicular to the outer face 102B of the molding web 102. The portions of the cavities 102C forming the rods 102C1 typically have a geometry of rotation about an axis perpendicular to the outer face 102B of the molding web 102, or a geometry having a plane of symmetry extending in a direction parallel to the direction of travel of the molding web 102 and/or in a direction perpendicular to the direction of travel of the molding web 102.

The portions of the cavities 102C forming the heads 102C2 typically extend radially or transversely with respect to an axis perpendicular to the outer face 102B of the molding web 102, and may have rotational symmetry about this axis perpendicular to the outer face 102B of the molding web 102. The portions of the cavities 102C forming the heads 102C2 typically have a substantially frustoconical or hexahedral shape.

The portions of the cavities 102C forming the heads 102C2 may be linear or curved, for example to form portions curved towards the inner face 102A or towards the outer face 102B of the molding web 102 extending from the portions of the cavities 102C forming the rods 102C1.

The portions of the cavities 102C forming the heads 102C2 may have a constant or variable thickness.

In the example represented in the figures, the portions of the cavities 102C forming the heads 102C2 extend radially around the portions of the cavities 102C forming the rods 102C1, and have a general disk shape.

The molding web 102 may have a particular texturing on its inner face 102A or on its outer face 102B such as slots, a groove network or a passage network forming a vent or spikes, or may be substantially smooth.

The molding web 102 may be formed by a superposition of several webs, and therefore is not necessarily in a single-piece or single-material.

The material distribution means 106 is typically disposed so as to carry out the injection of molding material into the molding web 102 in a section of the molding web 102 where the latter is bearing against a driving roller, in this case the driving roller 104A in the example represented in FIG. 3. The driving roller then forms a bottom for the cavities 102C.

In the case where the injection of molding material is carried out while the molding web 102 is not bearing against a driving roller, the material distribution means 106 may then comprise a base disposed on the other side of the molding web 102, so that the inner face 102A of the molding web 102 is bearing against the base when the injection of material is carried out, the base then forming a bottom for the cavities 102C of the molding web 102.

The use of a molding web 102 associated with driving means 104 compared to the use of conventional formation means such as rollers in which molding cavities are directly produced is advantageous for several reasons.

The use of a molding web 102 is in particular interesting in terms of modularity. The molding web may indeed be easily removed and replaced by the driving means, unlike a solid roller for which the demounting and remounting operations are particularly complex to perform. Such an advantage is particularly observed when the two rollers 104A, 104B are fixed to a frame on one and the same side, leaving the end of the other side free to introduce/remove the molding web. A means for guiding the molding web may also be used in order to facilitate the introduction and/or removal thereof.

In addition, the production of a molding web is greatly simplified compared to the production of a roller including molding cavities. Such rollers are indeed typically produced by stacking of successive slices, therefore requiring multiple machining operations and causing significant constraints during assembly and at each change of hook reference and has a significant mass requiring the maintenance of these rollers by their two ends, which therefore complicates their replacement.

The cavities 102C in the molding web 102 may be produced by an etching process or by the use of a laser at the places where it is desired to form retention elements 16. It is also possible to envisage producing the molding web 102 with cavities 102C distributed uniformly over the entire molding web 102 and then plugging the cavities 102C at the places where it is desired to form zones 20 free of retention elements 16.

In FIG. 3, reference C identifies the separation between the tape 26 and the molding web 102, this point corresponding for example to the level from which the base 12 of the tape 26 is no longer in contact with the molding web 102. It may be provided that the molding web 102 supports the demolding roller 108, that is to say the demolding roller 106 forms a lever in the molding web 102 to facilitate the demolding of the preforms and/or hooks.

In the example represented, the cavities 102C of the molding web 102 are through cavities. The apparatus may then comprise an element, such as a scraper 110, positioned so as to scrape the inner face 102A of the molding web 102 to remove, if necessary, the excess molding material. It is meant by "injection" the action of shaping a melt molding material, for example, the distribution, the supply, the molding, the injection, the extrusion.

The apparatus presented above and the associated method may also have means for and a step of associating a non-woven (or woven) web 22 with the base 12.

Such an association of a web 22 on a base 12 including retention elements 16 is typically carried out by means of an adhesive, or via a melting of the base or of the web.

In order to secure a web 22, for example in non-woven, to the base 12 of the retention device 10, the proposed apparatus 100 may comprise web 22 driving means, adapted to achieve a web supply and to apply the web against the lower face 12B of the base 12 downstream of the material distribution means 106.

Figure 4:
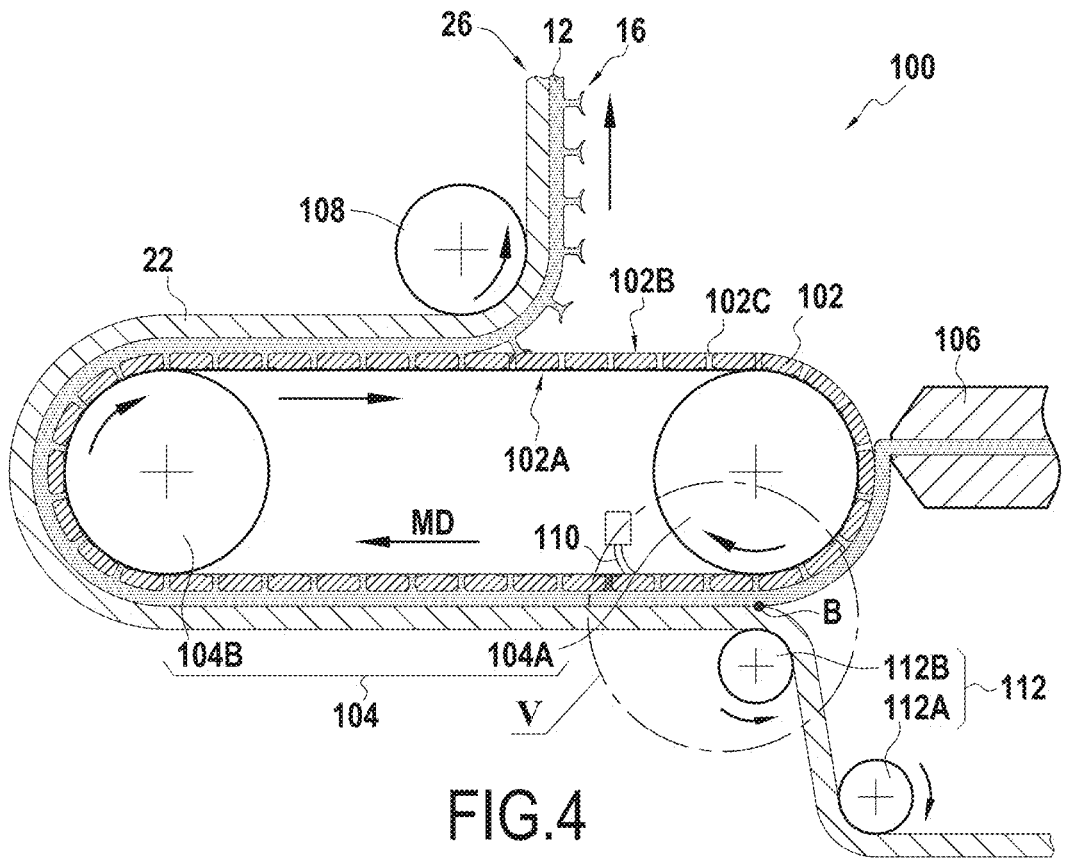
FIGS. 4 and 5 are schematic representations of an example of apparatus for producing a retention device including a woven or non-woven web.
Figure 5:
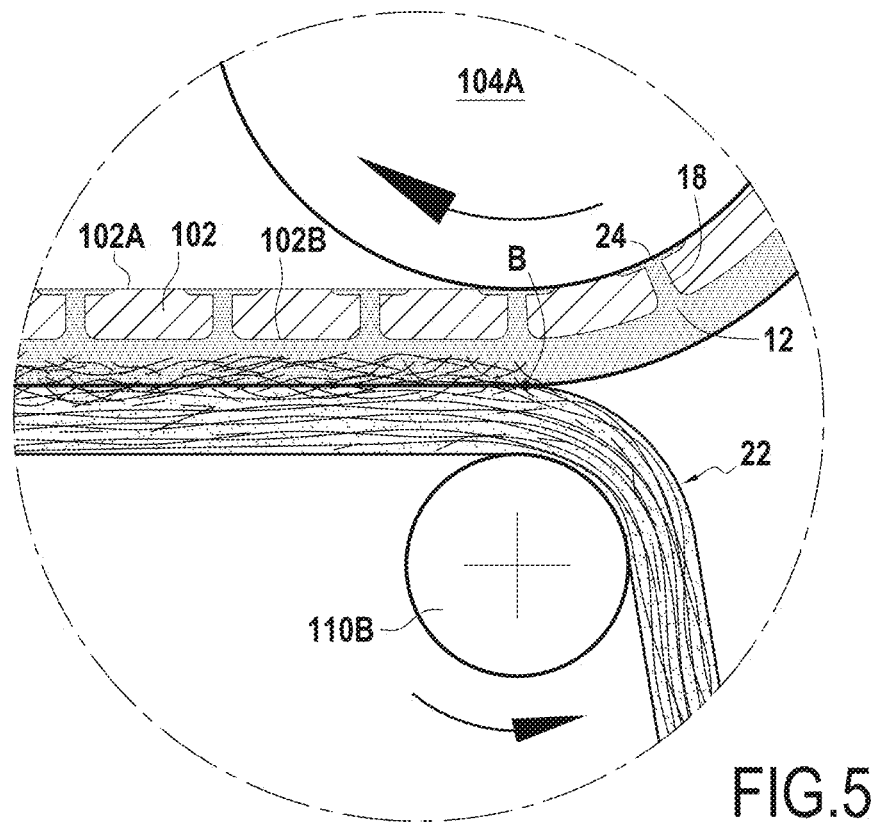

FIGS. 4 and 5 schematically represent an example of apparatus 100 including such means.

The apparatus as illustrated is similar to the one presented previously with reference to FIG. 3; the elements in common are therefore not described again here.

As can be seen in FIGS. 4 and 5, the apparatus as presented includes web driving means 112, here made up of two rollers 112A, 112B, configured to achieve a web supply 22 downstream of the material distribution means 106.

The web 22 is typically a layer of non-woven material, a thermoplastic film, an elastic film or a composite film, or a set of thermally consolidated fibers and/or filaments. The web 22 is for example a lap of fibers and/or filaments.

In the example represented in FIGS. 4 and 5, the web is represented as a layer of non-woven material.

The substrate driving means 110 are configured to supply the apparatus with web 22, and apply this web 22 against the lower face 12B of the base 12 downstream of the material distribution means 106.

The substrate driving means 110 are configured so that this application is carried out prior to the solidification of the base 12. Thus, this application causes at least partial penetration of the web 22 beyond a plane defined by the lower face 12B of the base 12. The reference B in the figures identifies the point of contact between the base 12 and the web 22.

More specifically, the lower face 12B of the base 12 is substantially planar, and defines a plane. The application of the substrate against this face causes a penetration of portions of the web 22, for example of fibers and/or filaments of the layer of non-woven material in the case where the web 22 is a layer of non-woven material within the base 12, thereby passing through the lower face 12B of base 12.

Insofar as such an application is carried out prior to the solidification of the base 12, it is not necessary to heat the base 12 and/or the web 22 in order to make such a bond.

By way of example, by considering a base 12 made of polypropylene, the application of the substrate against the lower face 12B of the base 12 is typically carried out when the lower face 12B of the base 12 has a temperature comprised between the melting temperature of the material and the Vicat softening temperature B of the material constituting it minus 30° C. (degree Celsius) or between the melting temperature of the material constituting it and the Vicat softening temperature A of the material constituting it. More particularly, when the base includes a polypropylene-based material, the lower face 12B of the base 12 has a temperature comprised between 75° C. and 150° C., typically on the order of 105° C., this temperature being typically measured by mans of an infrared or laser camera. It is meant by "VICAT softening temperature" the temperature obtained according to one of the methods described in the standards ISO 306 or ASTM D 1525 with a heating rate of 50° C./h and a normalized load of 50N for the VICAT B and a normalized load of 10N for the VICAT A.

The web 22 may be applied in a uniform or non-uniform manner against the lower face 12B of the base 12.

The bond made between the web 22 and the base 12 may be made in a uniform or non-uniform manner.

In the case where the web 22 is a set of thermally consolidated fibers and/or filaments, the bond with the base 12 is also made by penetration into the base 12 of part of the fibers and/or filaments of the web 22.

In the case where the web 22 is a set of thermally consolidated fibers and/or filaments, a thermoplastic film, an elastic film or a composite film, a phenomenon of shrinkage of the base 12 during its cooling may then result from the bond with the base, this shrinkage promoting the binding surface between the substrate and the base of the tape. This shrinkage has no impact on the visual appearance for the final user.

In the case where the web 22 is a layer of non-woven material, the demolding of the hooks is carried out easily even with a non-woven whose grammage is less than 80 g/m² (mass of material in grams per non-woven square meter). For example, the non-woven grammage may be comprised between 5 g/m² and 120 g/m², or between 25 g/m² and 100 g/m², or between 10 g/m² and 70 g/m².

In the case where the web 22 is a layer of non-woven material, the apparatus may comprise a calendering device upstream of the substrate driving means 112, thus making it possible to perform a step of locally or non-locally calendering the layer of non-woven material prior to its application against the base 12.

This mode of securing a web 12 to a base 12 including retention elements 16 is in particular advantageous in that it does not cause deformation of the base 12, and therefore advantageously allows keeping the shape of the base 12 obtained during the injection step, and in particular keeping the straight edges obtainable via the method and the apparatus described above.

This mode of securing a substrate to a tape may be applied to a tape forming method as described above, or more generally to any other tape forming method including retention elements such as hooks.

Figure 6:
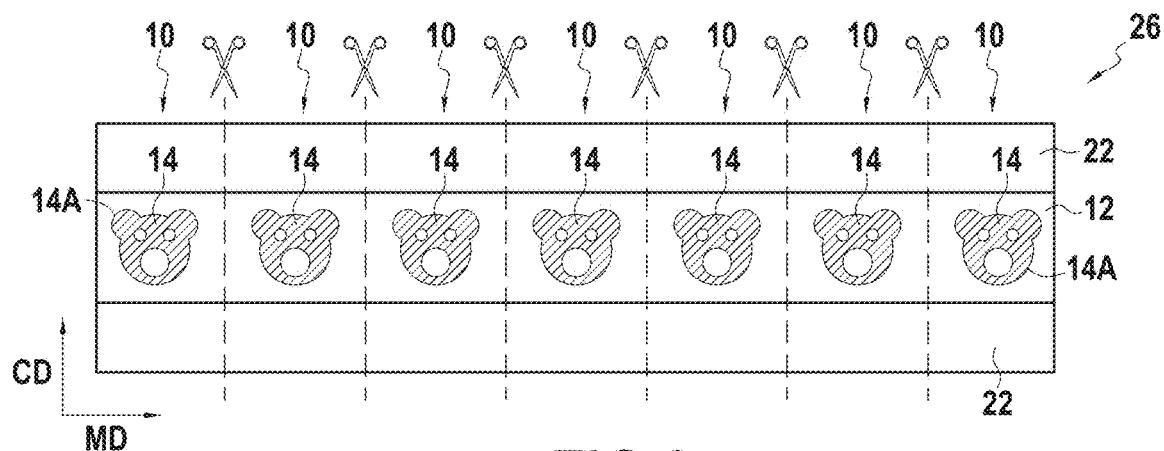
FIG. 6 is a top view in schematic representation of part of a tape for a retention device.

FIG. 6 schematically represents part of a tape 26 obtained by means of the apparatus 100 of FIG. 4.

The tape 26 is intended to be cut into a plurality of retention devices 10. The location of the cutouts is represented by the dotted lines in FIG. 6. The tape 26 and each retention device 10 includes a continuous base 12 made of thermoplastic material and retention elements 16 forming patterns 14. In this embodiment, the patterns 14 are the patterns 14 of FIG. 1C.

Figure 7:
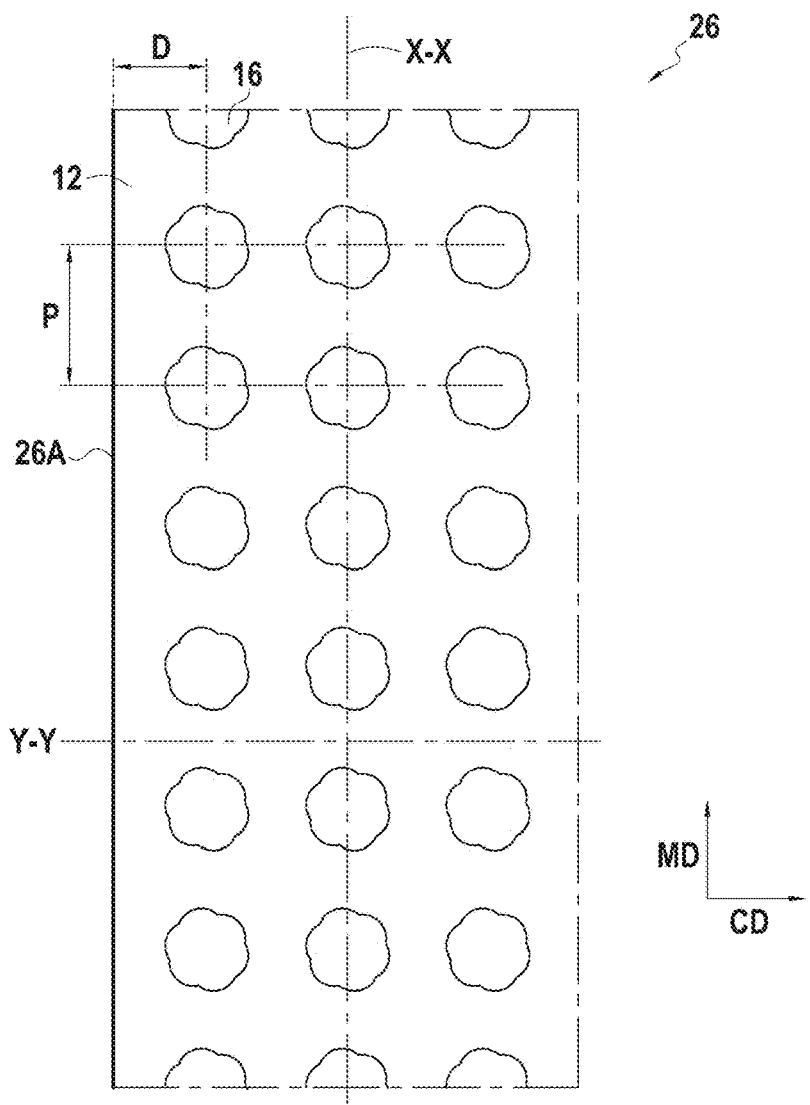
FIG. 7 is a top view in schematic representation of another tape for a retention device.

FIG. 7 represents a tape 26 in top view, which tape 26 includes a base 12 and retention elements 16, here preforms or hooks. For simplicity, the retention elements 16 have been enlarged and are represented distributed uniformly on the base 12.

FIG. 7 schematically represents the tape 26 obtained with the apparatus 100 of FIG. 3. The tape 26 therefore extending in a longitudinal direction identified by an axis XX in FIG. 7, which is parallel to the direction MD. FIG. 7 also represents the transverse direction, identified by an axis YY, which is parallel to the CD direction.

For this tape 26, an edge 26A extending in the MD direction is defined, this edge 26A defining one of the two ends of the tape 26 in the CD direction.

The retention elements 16, including a rod 8 surmounted or not by a head 24, are generally arranged in the vicinity of the edge 26A. The retention elements 16 are typically arranged at a distance D from the edge 26A comprised between 2 and 3 pitches P between the retention elements, typically equal to 2 or 3 pitches P of the retention elements, the distance D being measured in the transverse direction relative to the longitudinal direction materialized by the axis XX in FIG. 7. The pitch P between two retention elements 16 corresponds to the distance between the center of two successive retention elements in the longitudinal direction. In the example represented in FIG. 7, the retention elements 16 are arranged in columns extending in the longitudinal direction materialized by the axis XX, these columns being repeated identically in the transverse direction.

It will be noted that FIG. 7 is not a scale representation. Indeed, the distance D between an edge 26A and the first retention element 16 is represented as being less than the radius R of the circle 28 corresponding to the average pitch. The center of each circle is positioned, when viewed from above, over the center of each retention element and the circumference of a first circle passes through the center of an adjacent retention element. The average pitch may correspond to the distance separating two adjacent retention elements, i.e. the radius R of the circle 28. However, the distance D is typically equal to 2 or 3 average pitches. The diameter (equal to two times the radius R) in which the retention element is inscribed (viewed from above, perpendicularly to the retention element) is greater than or equal to 80 µm, preferably greater than or equal to 250 µm and less than or equal to 500 µm, preferably less than or equal to 450 µm.

It will be noted that on the left side of FIG. 7, the retention device 10 does not include a zone free of retention element 16 within the meaning of the present disclosure. Indeed, the distance D defines a rectilinear web along the edge 26A of the base 12 free of retention elements. However, this web does not allow defining a pattern within the meaning of the present disclosure, in that this web is not bordered on each side, in the direction perpendicular to the edge, by retention devices.

Figure 8:
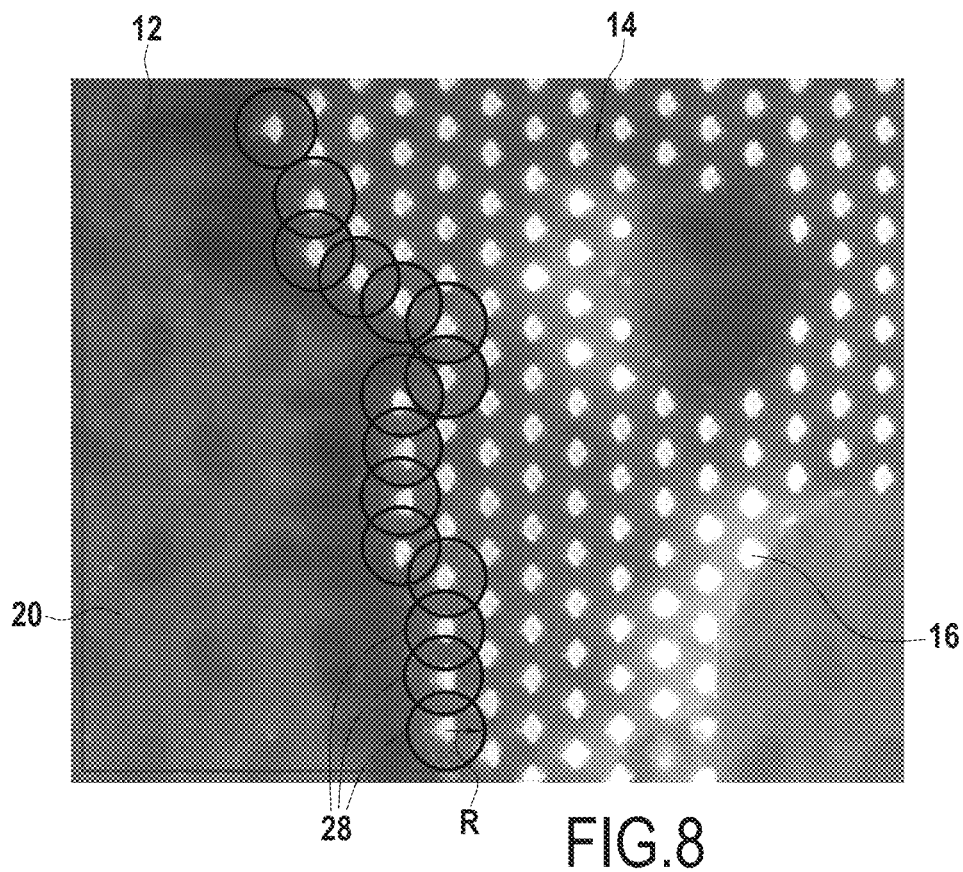
FIG. 8 is an enlarged partial view of the pattern of FIG. 1C.

The retention elements 16 may also be arranged in a staggered or "honeycomb" manner, for example by shifting the columns of retention elements in the longitudinal direction, as for example represented in FIG. 8.

In FIG. 8, only a few circles have been represented on the left side of the figure.

It is understood that the molding web 102 has cavities 102C disposed so as to form the pattern 14 in FIG. 8.

It is understood that this type of retention device 10 may be obtained by apparatuses other than molding web apparatuses 102. However, it is understood that the production of a molding web 102 including cavities 102C distributed so that the retention elements 16 form a pattern 14 on the base 12 is easier than the production of a roller, for example. In addition, it is relatively easy to change the molding web 102 of the apparatus 100 of FIGS. 3 to 5 when it is desired to produce a different pattern 14.

By way of non-limiting example, the material injected by the material distribution means 106 to form the base 12 and the retention elements 16 may comprise a colorless thermoplastic material or a thermoplastic material with a dye. The thermoplastic material may in particular be polypropylene.

The dye may be for example a white dye, for example mention may be made of the reference 50PP marketed by CABOT and which is loaded at 50% by mass of $TiO_2$. As another dye, mention may also be made of a purple dye of reference UN55206 manufactured by COLOR SERVICE. These examples are given as non-limiting examples.

In all the examples mentioned, the density of the retention elements 16 in the pattern(s) 14 is equal to 280 retention elements 16 per cm² of base 12, the retention elements 16 having a pitch (center-to-center distance from two adjacent retention elements) between two retention elements equal to 0.64 mm. This density of retention elements is given by way of non-limiting example. The base 12 has a thickness E, measured perpendicularly to the upper face 12A of the base 12, equal to 60 μm (see FIG. 2). The retention elements 16 have a height H, measured perpendicularly to the base 12, which is 5 times the thickness of the base 12.

The height H of the retention elements may be greater than or equal to 35 μm, preferably greater than or equal to 55 μm, even more preferably greater than or equal to 80 μm and less than or equal to 500 μm, preferably less than or equal to 350 μm, even more preferably less than or equal to 120 μm.

For example, the height H of the retention elements may be comprised between 80 and 350 μm or between 55 and 120 μm.

The diameter of the retention element (viewed from above, perpendicularly to the retention element) is greater than or equal to 80 μm, preferably greater than or equal to 250 μm and less than or equal to 500 μm, preferably less than or equal to 450 μm.

Example 1 a mixture of polypropylene and white dye of reference 50PP marketed by CABOT and which is loaded at 50% by mass of $TiO_2$ may be injected. The injected mixture may comprise 99.2% by mass of polypropylene and 0.8% by mass of white dye.

Example 2 a mixture of polypropylene, purple dye of reference UN55206 manufactured by COLOR SERVICE and white dye of reference 50PP marketed by CABOT and which is loaded at 50% by mass of $TiO_2$ may be injected. The injected mixture may comprise 99.2% by mass of polypropylene, 0.4% by mass of white dye and 0.4% by mass of purple dye.

Example 3

Figure 9:
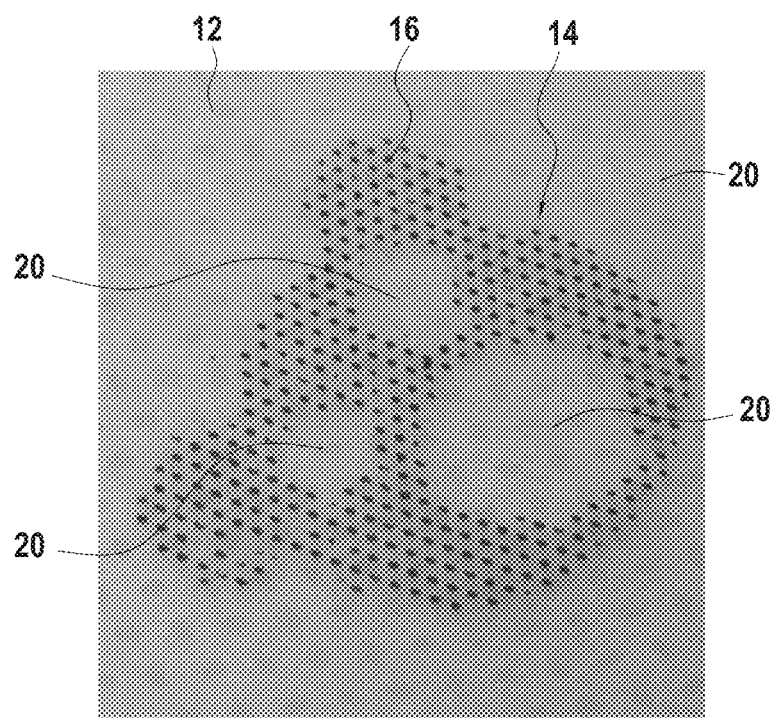
FIG. 9 is a view of a retention device including a colored coating.
Figure 10:
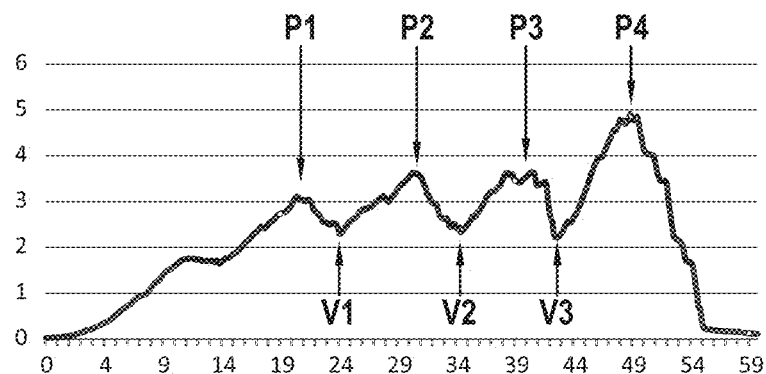
FIGS. 10 to 14 are graphs representing the peeling force expressed in Newton as a function of the opening stroke expressed in millimeters respectively for the patterns 1K-1O.
Figure 11:
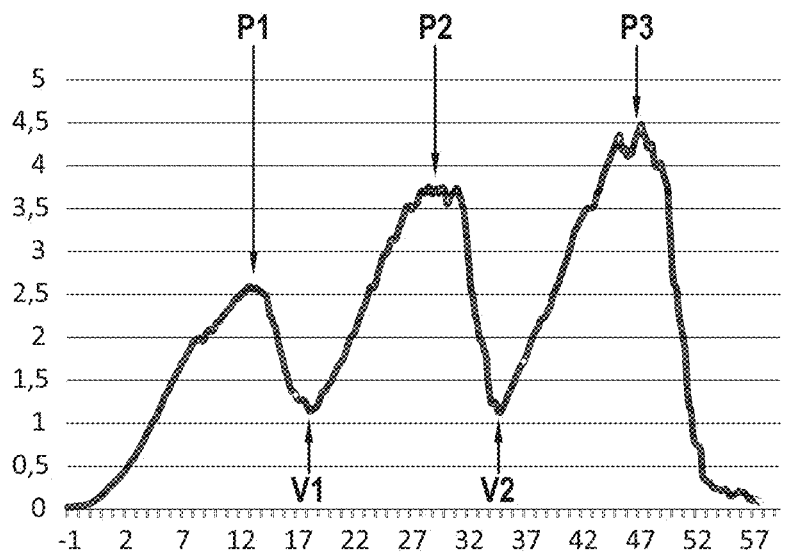
Figure 12:
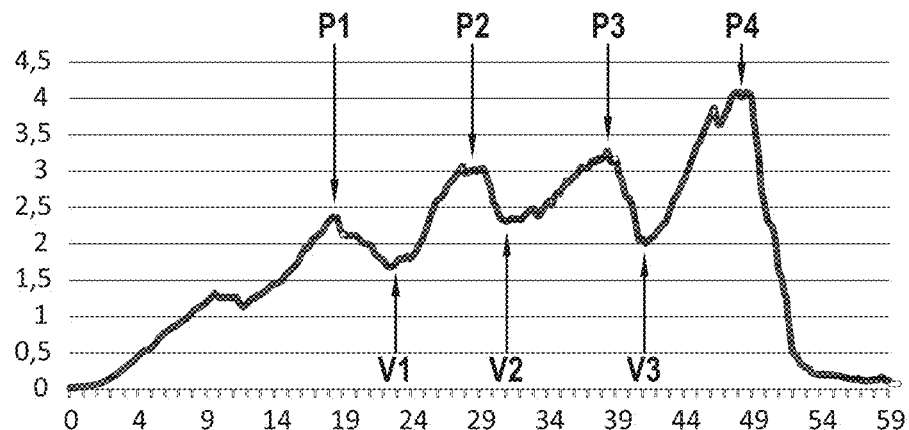
Figure 13:
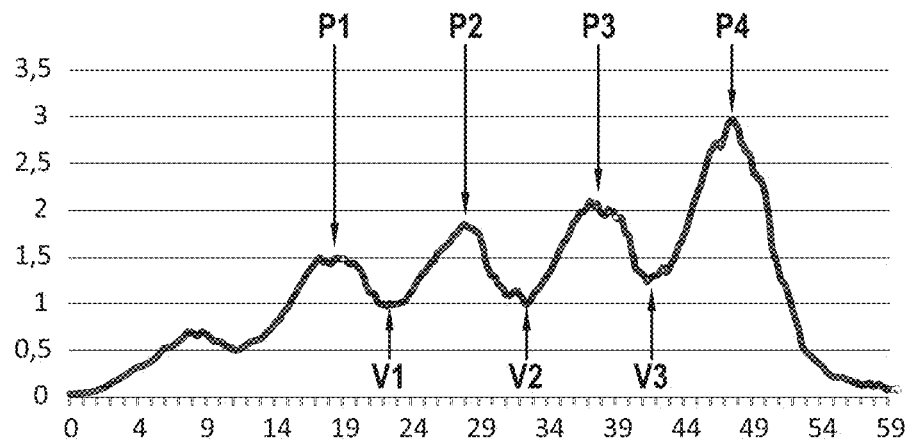
Figure 14:
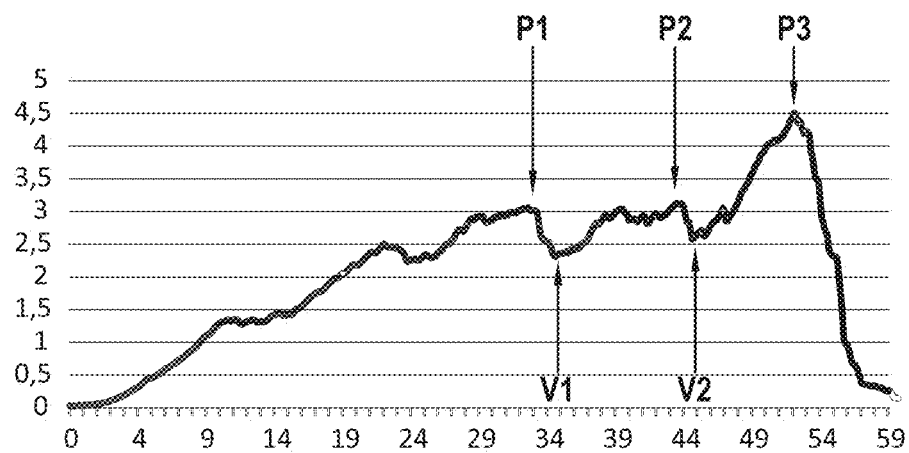

Example 3 presents the same composition as Example 1 and includes a colored coating which is deposited on the retention elements 16 by using an ink and/or a dye, such as those commonly used in flexography and/or in pad printing, for example a black ink, as represented in FIG. 9.

Example 4

Example 4 presents the same composition as Example 2 and includes a colored coating which is deposited on the retention elements 16 by using an ink and/or a dye, such as those commonly used in flexography and/or in pad printing, for example a black ink, as represented in FIG. 9.

In the CIE L*a*b* space, the parameters L*, a* and b* are measured respectively for zones 20 free of retention elements and parts of the pattern 14 formed by the retention elements 16. The values of L*, a* and b* are measured for example with a spectrocolorimeter in natural light (under the reference D65/10°) of model RM200QC of x-rite pantone on a white support and the color difference ΔE* between the zones 20 free of retention elements and at least part of the pattern 14 formed by the plurality of retention elements 16 is calculated according to equation (1).

For the example 1, the color difference ΔE* is equal to 1.606; for the example 2, the color difference ΔE* is equal to 5.493; for the example 3, the color difference ΔE* is equal to 7.352 and for the example 4, the color difference ΔE* is equal to 7.911.

It is understood that the color difference is present on the retention devices as soon as the base 12 includes zones 20 free of retention elements 16. Thus, the color difference between the zones 20 free of retention elements and at least part of the pattern 14 formed by the plurality of retention elements 16 allows improving the actual feeling/quality and/or the feeling/quality perceived by the user when a user uses the retention device in a closing and/or opening manner. It is understood that this advantage may be obtained independently of the shape of the pattern 14.

In the CIE XYZ color space, the difference in opacity between the zones 20 free of retention elements and at least part of the pattern 14 formed by the plurality of retention elements 16 is measured for example with a natural light spectrocolorimeter (under the reference D65/10°) of model RM200QC of x-rite pantone. The values of $Y_{black\ background}$ et $Y_{white\ background}$ are measured on a white support and on a black support respectively for the zones 20 free of retention elements and at least part of the pattern 14 formed by the plurality of retention elements 16 and the opacity expressed in % is calculated according to equation (2) respectively for the zones 20 free of retention elements and at least part of the pattern 14 formed by the plurality of retention elements 16.

The difference in opacity between the zones 20 free of retention elements and at least part of the pattern 14 formed by the plurality of retention elements 16 is equal to the absolute value of the difference in opacity values obtained for the zone 20 free of retention elements and for at least part of the pattern 14 formed by the plurality of retention elements 16.

For the example 1, the opacity difference is equal to 0.45; for the example 2, the opacity difference is equal to 3.67; for the example 3, the opacity difference is equal to 1.87 and for the example 4, the opacity difference is equal to 12.00.

As can be observed, the opacity difference allows improving the perception of the color difference ΔE* perceived by the user. Indeed, for the example 1, the color difference ΔE* being greater than 1, the user may see a difference between the zones 20 free of retention elements and the pattern 14. However, the differentiation between the zones 20 free of retention elements and the pattern 14 is better for the example 2 for which the color difference ΔE* is equal to 5.493 and the opacity difference is equal to 3.67.

The patterns 14 of FIGS. 1A-1O are generally used in the CD direction, that is to say the peeling, i.e. the separation of the retention device 10 from a loop application zone for example is made parallel to the CD direction.

The patterns 14 of FIGS. 1A-1D could also be pivoted by 90°.

The pattern 14 of FIG. 1E is preferably used as represented in this figure. Indeed, the shape of the pattern 14 being substantially like a "V", the separation of the retention device 10 of an application zone transforms the force applied in the CD direction to detach or separate the retention device 10 from an application zone into a peeling force component and into a shear force component. It is understood that the pattern 14 in FIG. 1E is arranged so that when the retention device 10 is biased in an opening manner, a force exerted on the retention device 10 is divided between at least a first peeling force component and a second shear force component. The same applies for the pattern in FIG. 1F.

It will be noted that the patterns 14 in FIGS. 1K to 1O have, in the CD direction, an alternation of zones 20 free of retention elements 16 and of patterns 14 and also, in the MD direction, continuous zones 20 free of retention elements 16.

For the patterns 1K to 1O, FIGS. 10 to 14 respectively represent the peeling curves obtained with the "180° peeling" method by using an application zone 30 marketed by APLIX under the reference "SoftLoop Premium by APLIX", including a loop non-woven of the carded thermally-bonded type and an SMS non-woven assembled by hot calendering.

The peeling curves present the peeling force expressed in N (ordinate) as a function of the opening stroke expressed in millimeters (abscissa). The curves presented in FIGS. 10 to 14 are averages made on 20 measurements of different samples. The peeling direction is parallel to the CD direction for all of the retention devices tested.

The retention devices 10 according to the patterns in FIGS. 1K to 1O are prepared in accordance with the "180° peeling" method described above.

Figure 15:
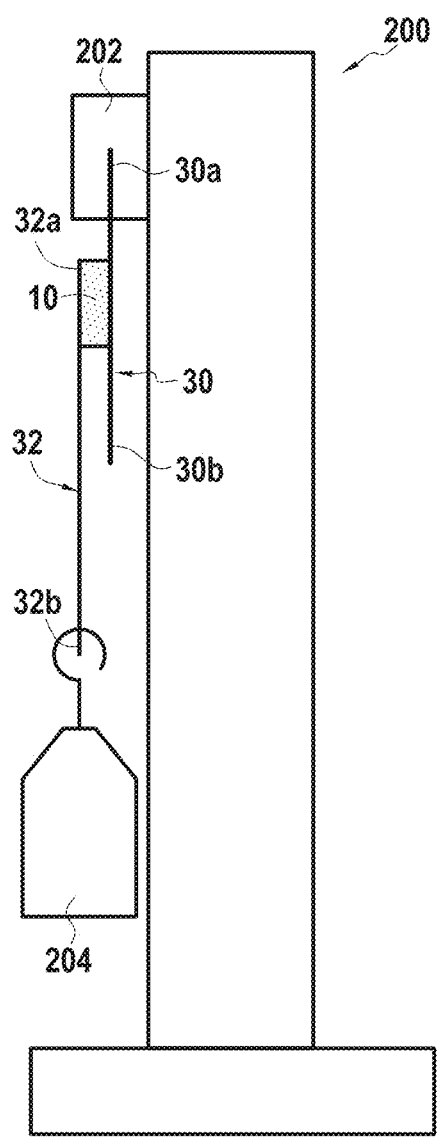
FIGS. 15 and 16 are schematic representations of equipment used to measure the peeling force.
Figure 16:
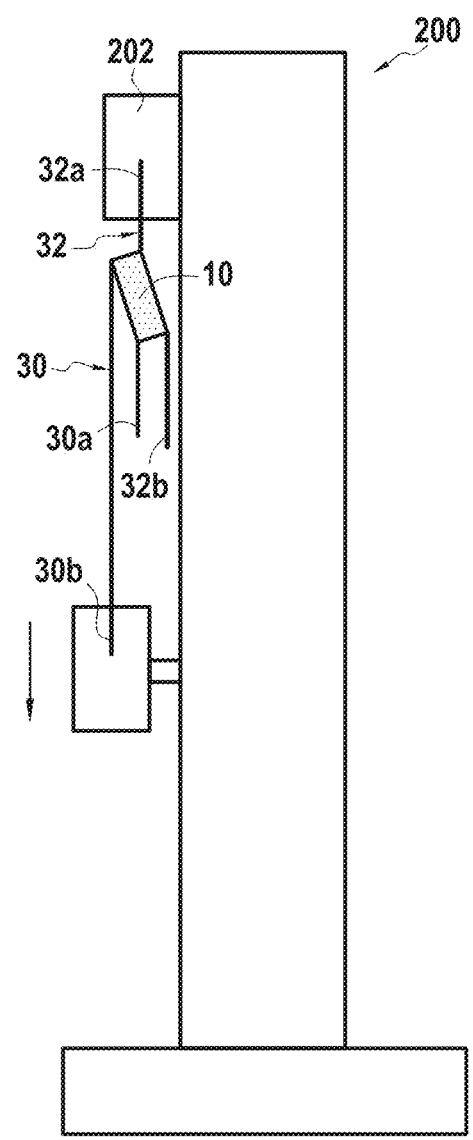

FIG. 15 represents a strip 32 including the retention device 10 to be tested, the retention device being assembled on the application zone 30. The sample from the application zone 30 is disposed in a clamp 202 of a bellows 200, the cut side 30a being in the clamp 202 and a weight 204 of 1 kg is suspended from the lower part 32b of the strip 32 for 10 s (second). The weight 204 is then removed.

The assembly is then disposed in a tensile-testing machine 210 including a measuring cell of 100 N. The end 32a of the strip 32, that is to say the end opposite to the lower part 32b, is inserted into the upper jaw 212. The reading of the force measuring cell is set to zero. The cut end 30a of the sample from the application zone 30, that is to say the side opposite to the uncut side 30b) is inserted into the lower jaw 214 and a slight tension is created. The force must be comprised between 0.02 N and 0.05 N. During installation, the jaws 212, 214 are spaced apart from each other by 50 mm. The assembly is centered between the two jaws 212, 214. The test is carried out at constant movement at a speed of 305 mm/min (millimeter per minute) and the test stroke is of 50 mm. This test stroke is adjusted as a function of the width of the retention device to be tested so as to allow total separation of the retention device and of the application zone.

As can be observed in FIGS. 10 to 14, the peeling curves have successive peaks P1-P4, each peak having a maximum value greater than the maximum value of the peak which precedes it in the direction of the opening stroke, i.e. between two consecutive peaks taken two by two, the maximum value of the peak with the largest abscissa is greater than the maximum value of the peak with the smallest abscissa, and vice versa, the maximum value of the peak with the smallest abscissa is less than the maximum value of the peak with the largest abscissa. Thus, in FIG. 10, the maximum value of the peak P1 is less than the maximum value of the peak P2; the maximum value of peak P2 is less than the maximum value of the peak P3; the maximum value of the peak P3 is less than the maximum value of the peak P4. It will also be noted that the minimum value of the valleys V1-V3 is less than 50% of a maximum value of the peeling force, that is to say the maximum value of the peak P4.

The same applies for the patterns in FIGS. 1L-1N.

The peaks and valleys have a tip and a base, the base may have a width preferably greater than 1 mm, more particularly a width greater than 2 mm, in some cases, a width greater than 3 mm.

Thanks to the peeling force which has at least two consecutive peaks separated by a valley, the value of the peaks of the peeling force increasing with the opening stroke, the user feels this increasing force required to separate the retention device from the application zone. He therefore perceives that the retention device was well maintained on the application zone. Furthermore, the maximum value of the peeling force is such that the retention device may not detach from the application zone in an undesired manner.

It can be observed that for the pattern in FIG. 1O, the valley V2 has a minimum value which is greater than 50% of the maximum value of the peak P3. It is also observed that the different peaks P1-P3 are not marked as identifiable as on the other curves (FIGS. 10 to 13). This is in particular linked to the width L measured in the CD direction of the continuous zones 20 free of retention elements 16 in the MD direction.

It is understood that the peeling curves also depend on the nature of the application zone 30. However, application zones different from the application zone marketed by APLIX under the reference "SoftLoop Premium by APLIX" will give peeling curves with a similar profile, although the values of the peeling force may vary depending on the application zone.

It is understood that the peeling curves are independent of the color and/or of the color difference ΔE* between the zones 20 free of retention elements and at least part of the pattern 14 formed by the plurality of retention devices 16.

However, these two characteristics may be combined to improve the real feeling/quality and/or the feeling/quality perceived by the user when a user uses the retention device in a closing and/or opening manner.

Although the present disclosure has been described with reference to a specific exemplary embodiment, it is obvious that various modifications and changes may be made to these examples without departing from the general scope of the invention as defined by the claims. In addition, individual characteristics of the various embodiments mentioned may be combined in additional embodiments. Consequently, the description and the drawings should be considered in an illustrative rather than restrictive sense.

The present disclosure may find application in the field of hygiene, diapers, adult incontinence, packaging industry, for example food packaging, ostomy, buildings and the like.

The invention claimed is:

1. A retention device comprising:
   a continuous base having an upper face and a lower face; and
   a plurality of retention elements extending from the upper face of the base, each retention element comprising a rod;
   the base including at least one zone free of retention elements so that the plurality of retention elements form at least one pattern, and wherein the pattern is repetitive in a peeling direction, the peeling force measured according to the "180° peeling" method having at least two peaks and at least one valley comprised between the two peaks, maximum values of the peaks increasing as peeling progresses and the at least one valley having a minimum value less than or equal to 85% of a maximum value of the peeling force.

2. The retention device according to claim 1, the peeling force measured according to the "180° peeling" method has at least three peaks and at least two valleys, each valley being comprised between two consecutive peaks, the maximum values of the peaks increasing as peeling progresses and the valleys having a minimum value less than or equal to 85% of a maximum value of the peeling force.

3. The retention device according to claim 2, wherein the peaks and valleys have a tip and a base, the base having a width greater than 1 mm.

4. The retention device according to claim 2, wherein the peeling force is greater than or equal to 1.8 N.

5. The retention device according to claim 1, wherein the device comprises zones free of retention elements that are continuous in a direction perpendicular to the peeling direction.

6. The retention device according to claim 5, wherein the zones free of retention elements that are continuous in a direction perpendicular to the peeling direction have a width measured in the peeling direction greater than or equal to 2 rows of retention elements measured in the peeling direction.

7. The retention device according to claim 6, wherein the zones free of retention elements that are continuous in a direction perpendicular to the peeling direction have a width measured in the peeling direction greater than or equal to 3 rows of retention elements measured in the peeling direction.

8. The retention device according to claim 5, wherein the zones free of retention elements that are continuous in a direction perpendicular to the peeling direction have a width measured in the peeling direction greater than or equal to 1% of the width of the base measured in the peeling direction.

9. The retention device according to claim 1, wherein in a CIE L*a*b* color space, a color difference ΔE* between the at least one zone free of retention elements and at least part of the pattern formed by the plurality of retention elements is greater than or equal to 1.0.

10. The retention device according to claim 1, wherein the retention device includes the rod surmounted by a head.

11. The retention device according to claim 1, wherein a surface of the zones free of retention elements is greater than or equal to 5% of a total surface of the base.

12. The retention device according to claim 1, comprising a woven or non-woven web or a thermoplastic film or an elastic film or a composite film.

13. The retention device according to claim 1, wherein the base has a thickness, measured perpendicularly to the upper face of the base, comprised between 10 and 700 µm and a height of retention elements, measured perpendicularly to the upper face of the base, comprised between 3 and 10 times the thickness of the base.

14. A tape comprising a plurality of retention devices according to claim 1, positioned next to each other, the tape being intended to be cut at locations between the retention devices so as to obtain a plurality of individual retention devices.

15. The retention device according to claim 1, wherein the peaks and valleys have a tip and a base, the base having a width greater than 1 mm.

16. The retention device according to claim 1, wherein the peeling force is greater than or equal to 1.8 N.

17. The retention device according to claim 1, wherein the retention element is inscribed in a diameter which is greater than or equal to 80 µm.

18. The retention device according to claim 1, wherein a minimum distance between two retention elements is between 0.1 mm and 10 mm.

19. The retention device according to claim 1, wherein the pattern has a density of retention elements greater than or equal to 20 per cm$^2$.

* * * * *